(12) United States Patent
Gellman et al.

(10) Patent No.: US 8,518,058 B2
(45) Date of Patent: *Aug. 27, 2013

(54) SUTURE SYSTEM

(75) Inventors: Barry N. Gellman, North Easton, MA (US); Jozef Slanda, Milford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/284,267

(22) Filed: Oct. 28, 2011

(65) Prior Publication Data

US 2012/0041456 A1 Feb. 16, 2012

Related U.S. Application Data

(63) Continuation of application No. 12/510,464, filed on Jul. 28, 2009, which is a continuation of application No. 10/785,830, filed on Feb. 24, 2004, now Pat. No. 7,582,096, which is a continuation of application No. 09/939,114, filed on Aug. 24, 2001, now Pat. No. 6,719,764.

(51) Int. Cl.
*A61B 17/04* (2006.01)

(52) U.S. Cl.
USPC ........................................... 606/144

(58) Field of Classification Search
USPC .................. 606/139, 143, 144, 148
See application file for complete search history.

(56) References Cited

U.S. PATENT DOCUMENTS

| | | | |
|---|---|---|---|
| 3,840,017 A | 10/1974 | Violante | |
| 3,860,992 A | 1/1975 | Legg | |
| 4,557,265 A | 12/1985 | Andersson | |
| 5,037,433 A | 8/1991 | Wilk et al. | |
| 5,281,237 A | 1/1994 | Gimpelson | |
| 5,336,231 A | 8/1994 | Adair | |
| 5,364,408 A | 11/1994 | Gordon | |
| 5,387,221 A | 2/1995 | Bisgaard | |
| 5,391,174 A | 2/1995 | Weston | |
| 5,417,700 A | 5/1995 | Egan | |
| 5,454,823 A | 10/1995 | Richardson et al. | |
| 5,458,609 A | 10/1995 | Gordon et al. | |
| 5,470,338 A | 11/1995 | Whitfield et al. | |
| 5,527,321 A * | 6/1996 | Hinchliffe | 606/144 |
| 5,540,704 A | 7/1996 | Gordon et al. | |
| 5,540,705 A | 7/1996 | Meade et al. | |
| 5,562,689 A * | 10/1996 | Green et al. | 606/151 |
| 5,573,542 A | 11/1996 | Stevens | |
| 5,578,044 A | 11/1996 | Gordon et al. | |
| 5,591,179 A | 1/1997 | Edelstein | |
| 5,593,421 A | 1/1997 | Bauer | |
| 5,601,575 A | 2/1997 | Measamer et al. | |
| 5,607,435 A | 3/1997 | Sachdeva et al. | |
| 5,665,096 A | 9/1997 | Yoon | |
| 5,690,653 A | 11/1997 | Richardson et al. | |
| 5,700,273 A | 12/1997 | Buelna et al. | |
| 5,713,910 A | 2/1998 | Gordon et al. | |
| 5,741,279 A | 4/1998 | Gordon et al. | |
| 5,759,188 A | 6/1998 | Yoon | |
| 5,766,186 A * | 6/1998 | Faraz et al. | 606/145 |
| 5,779,718 A | 7/1998 | Green et al. | |
| 5,782,845 A | 7/1998 | Shewchuk | |

(Continued)

*Primary Examiner* — Darwin Erezo

(57) ABSTRACT

Sutures can be placed in difficult to access areas of the human body with devices, and related methods, utilizing a needle carrier. The devices and methods can be used in conjunction with both endosurgical and traditional open surgery procedures.

6 Claims, 7 Drawing Sheets

(56) References Cited

U.S. PATENT DOCUMENTS

| | | | |
|---|---|---|---|
| 5,827,298 A | 10/1998 | Hart et al. |
| 5,899,909 A | 5/1999 | Claren et al. |
| 5,904,692 A | 5/1999 | Steckel et al. |
| 5,908,428 A | 6/1999 | Scirica et al. |
| 5,911,727 A | 6/1999 | Taylor |
| 5,919,199 A | 7/1999 | Mers Kelly et al. |
| 5,954,732 A | 9/1999 | Hart et al. |
| 5,980,538 A | 11/1999 | Fuchs et al. |
| 6,048,351 A | 4/2000 | Gordon et al. |
| 6,117,067 A | 9/2000 | Gil-Vernet |
| 6,224,525 B1 | 5/2001 | Stein |
| 6,443,962 B1 | 9/2002 | Gaber |
| 6,454,778 B2 | 9/2002 | Kortenbach |
| 6,511,489 B2 | 1/2003 | Field et al. |
| 6,527,785 B2 | 3/2003 | Sancoff et al. |
| 6,551,329 B1 | 4/2003 | Kortenbach et al. |
| 6,719,764 B1 | 4/2004 | Gellman et al. |
| 6,955,643 B2 | 10/2005 | Gellman et al. |
| 6,997,932 B2 | 2/2006 | Dreyfuss et al. |
| 7,048,749 B2 | 5/2006 | Kortenbach et al. |
| 7,442,198 B2 | 10/2008 | Gellman et al. |
| 7,771,438 B2 | 8/2010 | Dreyfuss et al. |
| 2003/0208100 A1 | 11/2003 | Levy |
| 2006/0004385 A1 | 1/2006 | Gellman et al. |
| 2006/0178681 A1 | 8/2006 | Kortenbach et al. |
| 2007/0088372 A1 | 4/2007 | Gellman et al. |
| 2009/0062818 A1 | 3/2009 | Gellman et al. |

* cited by examiner

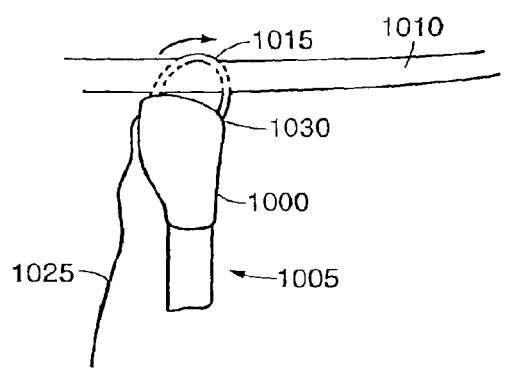
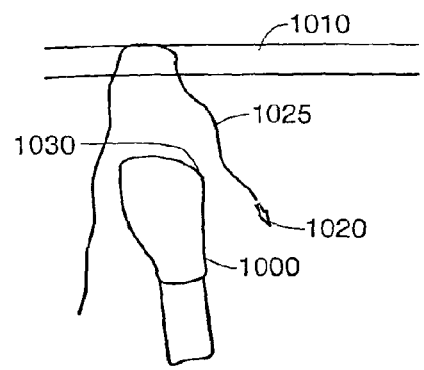
FIG. 10A  FIG. 10B
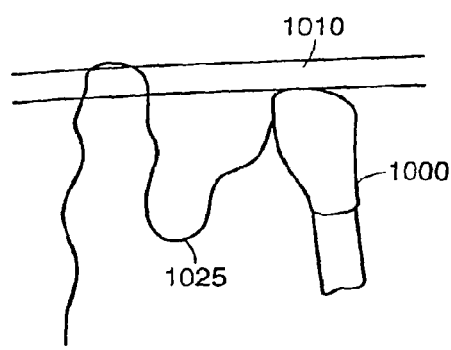
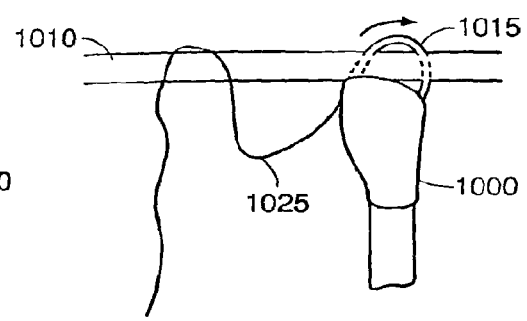
FIG. 10C  FIG. 10D
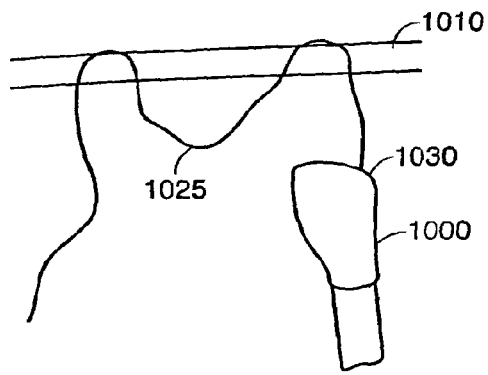
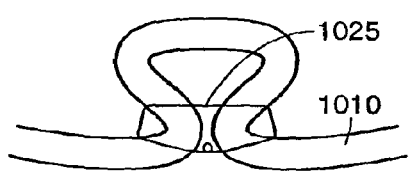
FIG. 10E  FIG. 10F

SUTURE SYSTEM

CROSS-REFERENCE TO RELATED APPLICATIONS

This application is a continuation application of U.S. patent application Ser. No. 12/510,464, filed on Jul. 28, 2009, which is a continuation application of U.S. patent application Ser. No. 10/785,830, filed on Feb. 24, 2004, now U.S. Pat. No. 7,582,096, which in turn is a continuation application of U.S. patent application Ser. No. 09/939,114 filed on Aug. 24, 2001, now U.S. Pat. No. 6,719,764. The entire contents of each of the above-referenced applications are incorporated herein by reference.

TECHNICAL FIELD

The invention relates to devices and methods for placing sutures.

BACKGROUND INFORMATION

Until recently, all but the simplest surgical procedures required the physician to make a large opening in the human body in order to expose the area requiring surgical repair. Today instruments are available that allow for viewing of internal body regions through a small puncture wound without exposing the entire body cavity. These instruments, called endoscopes, can be used in conjunction with specialized surgical instruments to detect, diagnose, and repair areas of the body that previously required open surgery to access.

Some surgical instruments used in endoscopic procedures are limited by the manner in which they access the areas of the human body in need of repair. In particular, the instruments may not be able to access tissue or organs located deep within the body or that are in some way obstructed. Also, many of the instruments are limited by the way they grasp tissue, apply a suture, or recapture the needle and suture. Furthermore, many of the instruments are complicated and expensive to use due to the numerous parts and/or subassemblies required to make them function properly. Suturing remains a delicate and time-consuming aspect of most surgeries, including those performed endoscopically.

SUMMARY OF THE INVENTION

The present invention allows for the performance of surgical procedures that involve the passing of sutures through tissue, for example, in a location that is facilitated by the suturing instrument deploying the suture in a forward-facing direction in relation to the suturing instrument. In addition, this invention provides for the catching and retrieval of the suture after it is passed through the tissue, for example. In particular this suturing instrument may be placed or positioned in the body such that a suture may be passed into a tissue of the body while the face of the distal end of the instrument abuts the tissue. Such a surgical device may allow for surgical procedures not previously possible or improve upon the performance of known surgical protocols.

In one aspect, the invention relates to a suturing instrument. The suturing instrument includes an elongate body member, a needle deployment system disposed at a distal portion of the elongate body member. The suture deployment system includes a forward-deploying needle carrier including a needle for tissue penetration and a catch to receive and retain the needle. The inclusion of a needle catch in the needle deployment system prevents the need for the introduction of a second surgical instrument into the location of the body where the suture was passed in order to retrieve the suture.

In some embodiments, the suturing instrument may include a deployment controller having a proximal end and a distal end. The deployment controller extends substantially along a longitudinal axis of the elongate body member to the distal portion of the elongate body member, where the distal end of the deployment controller is coupled to the needle carrier and moves the suture carrier between a retracted position and a deployed position. The proximal end of the deployment controller may be coupled to an actuator. In some embodiments, the deployment controller guides the suture carrier along a path which includes a proximal curved path segment such that the needle carrier initially travels away from the elongate body member and then toward the elongate body member.

Various embodiments according to the foregoing aspect of the invention can include the following features. A suture can include a needle, and the needle can be permanently fixed to an end of the suture. The needle fixed on the suture can insert into the needle carrier. Also, the needle can be plastic, metal, or polymer compound. In addition, the suturing instrument can include a catch to receive and retain the needle, where the catch is positioned on the body member such that a distal segment of the needle carrier's path is intercepted by the catch. Additionally, the suturing instrument may include a second needle carrier and a second forward-facing exit port. Further, the deployment controller may be coupled to the suture carrier with a flexible driver member. The flexible driver member may be manufactured of an alloy that includes at least or exclusively nickel and titanium.

In yet another embodiment, the invention relates to a suturing instrument including an elongate body member having a longitudinal axis and a distal tip needle deployment assembly joined with a distal end of the elongate body member such that the distal tip assembly is free to rotate axially about the longitudinal axis of the elongate body member. The distal tip suture deployment assembly includes a forward-facing needle exit port and a curved needle carrier channel formed in the distal tip needle deployment assembly, a curved needle carrier movably positioned in the curved needle carrier channel, a suture with an attached needle tip, and a deployment controller including a proximal end and a distal end. The deployment controller extends substantially along the longitudinal axis of the elongate body member to the distal end of the elongate body member, where the distal end of the deployment controller is coupled to the distal tip suture deployment assembly and moves the curved suture carrier through the curved suture carrier channel as the deployment controller moves between a retracted position and a deployed position. Additionally, the proximal end of the deployment controller may be coupled to an actuator.

In still another embodiment, the invention relates to a suturing instrument including a body member defining a forward-facing exit port and a carrier channel, a carrier movably positioned in the carrier channel, and a surgical needle attached with an interference fit on a distal end of the needle carrier. The needle carrier has a retracted position within an interior region of the body member and a deployed position exterior to the body member. The needle carrier is configured within the needle carrier channel such that the needle carrier exits the interior region of the body member through the forward-facing exit port. In addition, the forward-facing exit port, needle carrier channel, and needle carrier can be located in a distal tip assembly coupled to the body member, and the distal tip assembly can be coupled to the body member such that the distal tip assembly is free to rotate axially about a longitudinal axis of the body member. In addition, the needle carrier and needle catch can be located in a distal tip assembly coupled to the elongate body member at a pivot joint such that the distal tip assembly is free to deflect about the pivot joint. Such embodiments described above allow for enhanced control of the precise placement or position of the distal tip of the suturing instrument.

An additional aspect of the invention relates to a method for placing a suture in tissue. The method includes the steps of placing a suturing instrument enclosing a needle carrier having an attached needle for tissue penetration, deploying the needle carrier out of the suturing instrument through a forward-facing exit port such that the needle carrier exits an interior region of the suturing instrument through the exit port along a path which approaches being substantially tangential to an outer surface of the suturing instrument surrounding the forward-facing exit port, and capturing a needle attached to a suture and carried by the needle carrier in a catch that receives and retains the needle. The needle carrier is movably positioned within a needle carrier channel adjacent the tissue to be sutured.

In one embodiment, deploying the forward-deploying needle carrier out of the suturing instrument through a forward-directed exit port includes activating a deployment controller, which includes a distal end that extends substantially along a longitudinal axis of an elongate body member to the distal portion of the elongate body member. The distal end of the deployment controller is coupled to the needle carrier to facilitate movement of the needle carrier between a retracted position and a deployed position. In another embodiment, the invention further includes activating an actuator coupled to a proximal end of the deployment controller. In yet another embodiment, deploying the forward-deploying needle carrier out of the suturing instrument through a forward-directed exit port includes activating the deployment controller. The deployment controller is configured to guide the needle carrier along a path that includes a proximal curved path segment leading initially away from the elongate body member and then towards the elongate body member.

In yet another embodiment, the invention further includes placing a suturing instrument enclosing a second forward-deploying needle carrier. This embodiment may facilitate passing two sutures in the same general location without removing the surgical device from body in order to reload the needle carrier with a second needle. The needle carrier includes a needle and the second forward-deploying needle carrier is movably positioned within a needle carrier channel adjacent the tissue to be sutured. The needle may also include a suture attached to the needle. In another embodiment, the invention relates a method that includes the needle carrier following a path that includes a distal path segment. As the needle carrier traverses the distal path segment the needle is intercepted by the catch.

In another aspect, the invention relates to a method for shortening the pelvic floor including the steps of placing a suturing instrument enclosing a forward-deploying needle carrier including a needle adjacent to the tissue of the pelvic floor, deploying the suturing instrument such that the suture is passed through the tissue of the pelvic floor, and tightening the suture such that the pelvic floor buckles and is effectively shortened in height.

In one embodiment, the invention further comprises a second deploying of the suturing instrument such that the suture is passed through the tissue of the pelvic floor prior to tightening the suture such that the pelvic floor buckles and is effectively shortened in height.

In another embodiment, the invention relates to placing a suturing instrument enclosing a forward-deploying needle carrier including a needle adjacent to the tissue of the pelvic floor, in which the suturing instrument includes an elongate body member, a needle deployment system disposed at a distal portion of the elongate body member. The needle deployment system includes the forward-deploying needle carrier and a catch disposed on the elongate body member to receive and retain the needle. In yet another embodiment, the suturing instrument further includes a deployment controller that includes a distal end. The deployment controller extends substantially along a longitudinal axis of the elongate body member to the distal portion of the elongate body member, where the distal end of the deployment controller is coupled to the needle carrier to facilitate movement of the needle carrier between a retracted position and a deployed position.

These and other objects, along with advantages and features of the present invention herein disclosed, will become apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings.

FIGS. 10A-F illustrate a double suture-pass surgical method.

DETAILED DESCRIPTION

Embodiments of the present invention are described below. It is, however, expressly noted that the present invention is not limited to these embodiments, but rather the intention is that modifications that are apparent to the person skilled in the art are also included.

Figure 1:
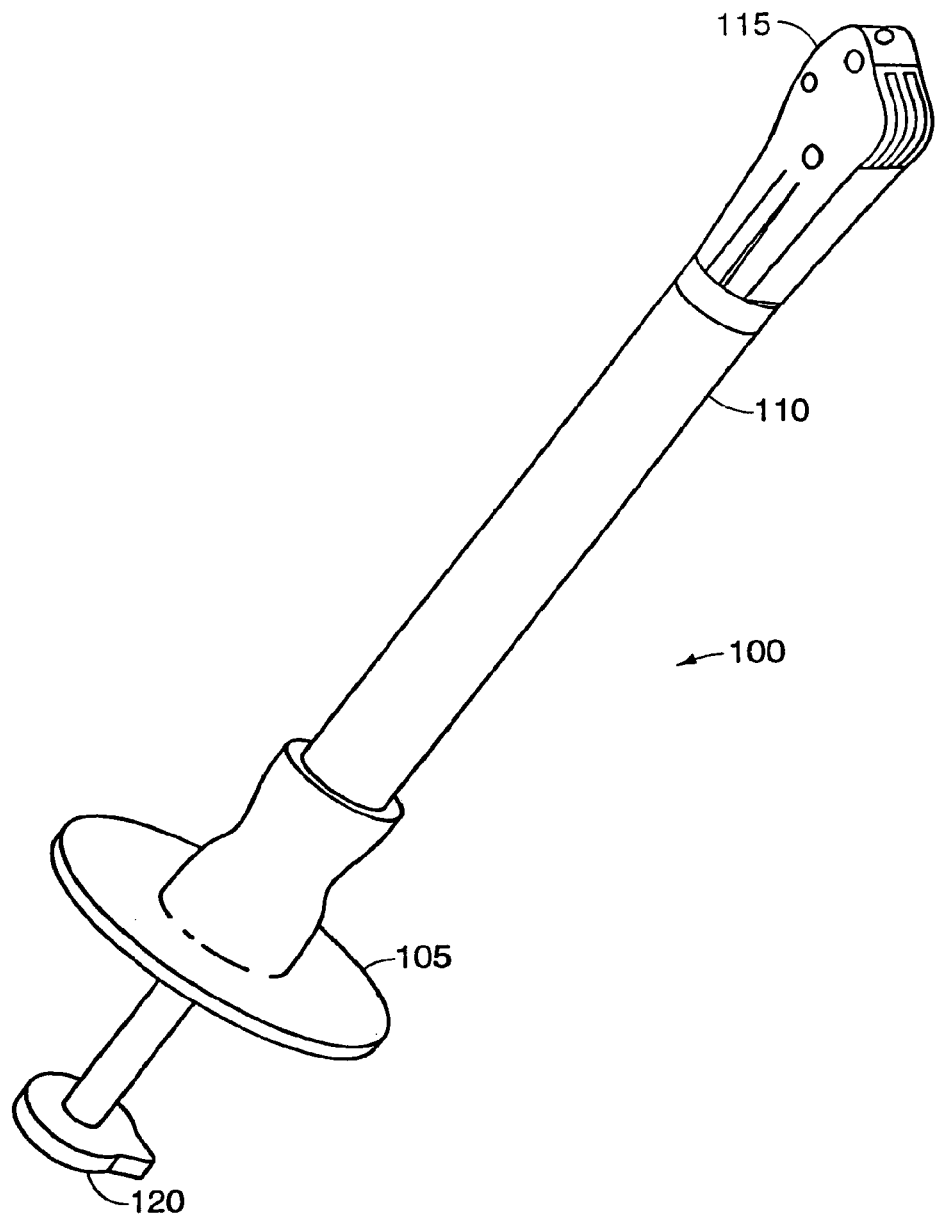
FIG. 1 is a perspective view of the general structure of one embodiment of the present invention.

FIG. 1 illustrates the general structure of one embodiment of the present invention. FIG. 1 depicts a suturing instrument 100 including handle 105, an elongate body 110, a distal tip 115, and an actuator button 120. This embodiment of the present invention is particularly well suited to, for example, the fixation of sutures to the pelvic floor during a procedure to effectively shorten the pelvic floor for the treatment of hypermobility. As will become apparent, this embodiment includes features that prevent the need for positioning the target tissue between the needle exit port and the needle catch on the side of a distal tip while placing the suturing instrument in the body. The embodiment of FIG. 1 allows for the positioning of the target tissue between the needle exit port and the needle catch on the front face of the distal tip during the placement of the suturing device into the body. The end of the distal tip 4 may be pressed against the target tissue in order to throw a suture into the tissue.

Figure 2:
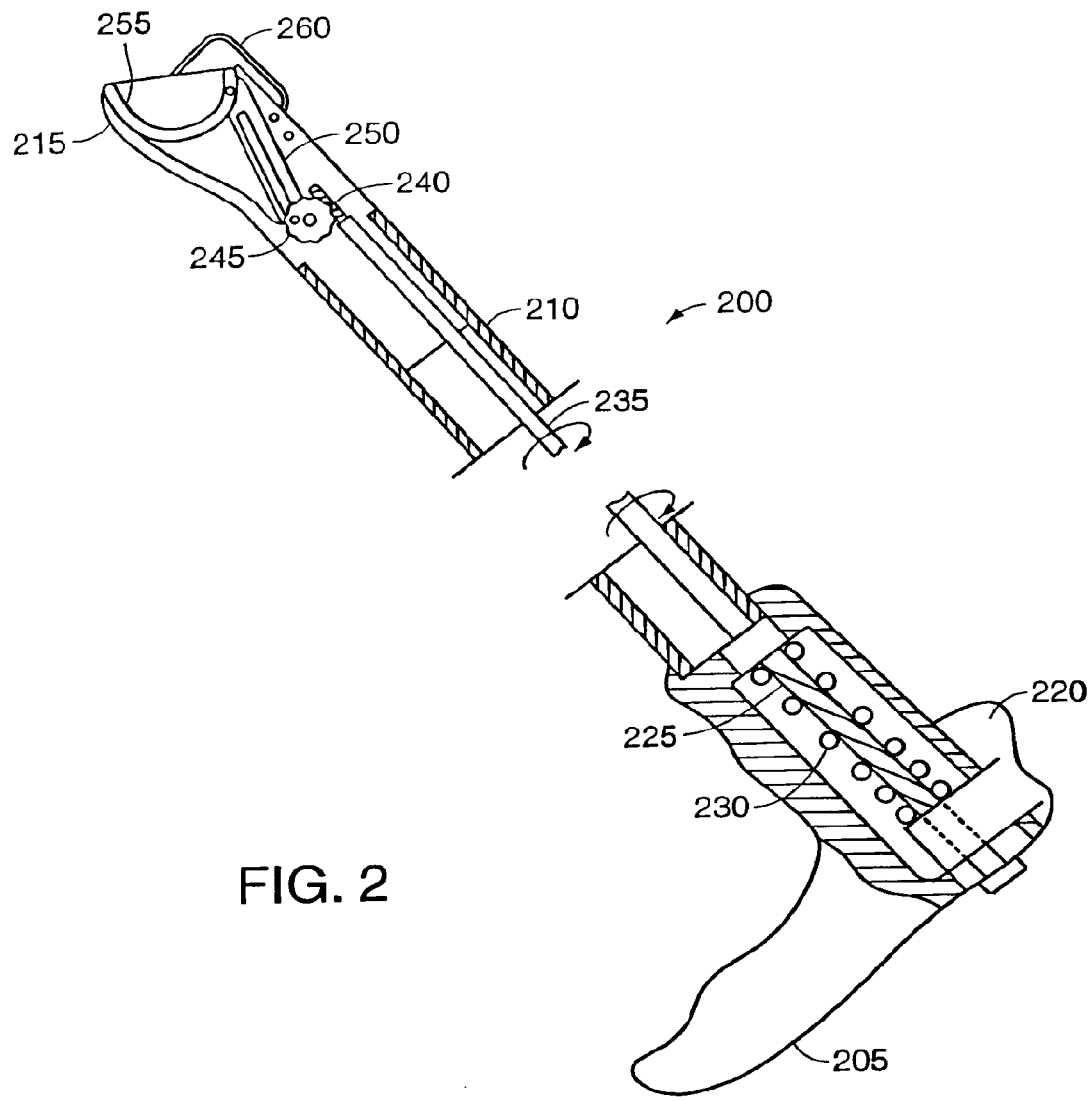
FIG. 2 is a partial-cutaway elevation of the general structure of another embodiment of the present invention.

FIG. 2 depicts an alternative embodiment of a suturing device 200, which includes a handle 205, an elongate body housing 210, a distal tip 215, and an actuator button 220. The button 220 operates a drive screw 225 and compression spring 230, which are housed in the proximal end of the body housing 210. The button 220 is mechanically linked to the drive shaft 235, which moves a gear drive 240, which in turn drives a gear 245. The gear 245 is coupled to a link drive pin 250, which is itself coupled to a needle carrier 255.

The needle carrier 17 shown in FIG. 2 is circular; however, it is contemplated that the above embodiment may be modified to include needle carriers having non-circular contours (e.g., helical, elliptical, or straight). Although a single needle carrier 255 is shown in the figure, the above configuration may in fact contain more than one needle carrier. For example, multiple needle carriers may be actuated and driven independently by dividing the deployment controls and the needle carrier drivers into separate adjacent members with separate handles or controlled by a single handle.

Figure 3:
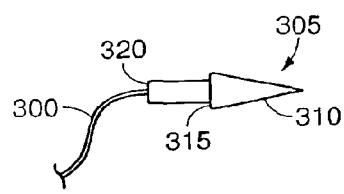
FIG. 3 is a side elevation view of a needle and suture.

Referring to FIG. 3, device 100, 200 according to the present invention may incorporate a length of suture material 300 with a needle tip 305. The needle tip 305 is held by a needle carrier 255. The needle carrier 255 and needle tip 305 are deployable out of the housing 110, 210 and into tissue. Deployment is via an actuator button 120, 220 coupled to rigid driving members which are suitably attached to the needle carrier 255. With renewed reference to FIG. 2, the actuator button 220 is pushed, simultaneously driving the needle carrier 255 and needle tip 305 into a catch mechanism 260. The needle carrier 255 is retracted back into the housing 210 and the needle tip 305 remain in the catch mechanism 260.

A needle tip 305 comprises a body 310 having a shoulder 315. The shoulder 315 is the rear surface of the needle tip body 310 that engages a catch 260 in the manner of a flange. A length of suture material 300 is inserted into a hole 23 located on the body 310 and attached to the needle tip 305 thereby. The suturing material 300 is attached to the body 310 by any suitable means, such as crimping or adhesive bonding. It should be understood that the illustrated arrow-shaped body 310 is merely illustrative, and the shape may be varied to fit a particular application. The needle tip 305 can be manufactured from a plastic, metal, or polymer compound and can be formed by, for example, extrusion, molding, or machining. Furthermore, the nature of the suture 300 is immaterial to the present invention. The needle tip 305 of the present invention may be used with a suture of any type, length, diameter, and characteristics.

Figure 4:
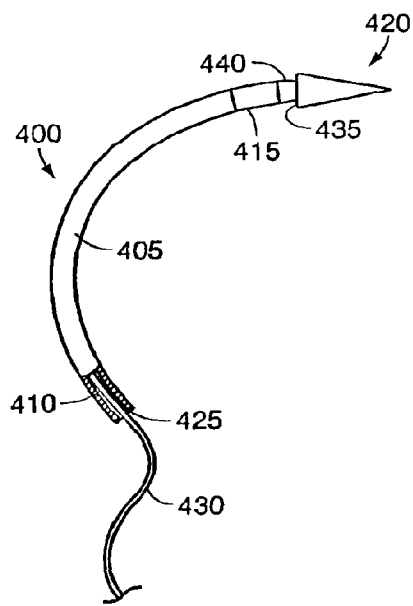
FIG. 4 is a partial-cutaway elevation of a needle with an attached suture in a needle carrier.

Referring now to FIG. 4, a needle carrier 400 comprises a body 405 defining a lumen 410, a needle holder 415 to receive a needle tip 420 for tissue penetration. The lumen 410 is in communication with the needle holder 415 at one end and with an aperture 425 at the other end. The needle holder 415 is sized and shaped to releasably engage the needle tip 420. A length of suture material 430 attached to the needle tip 420 is inserted into the needle holder 415, through the lumen 410, and out the aperture 425. The attached needle tip 420 is then releasably engaged with the needle holder 415. Alternatively, the needle carrier 400 can be a solid piece with the suture 430 disposed in a groove in the outer surface of the needle carrier 400.

The needle tip 420 is releasably engaged with the needle holder 415 so that the shoulder 435 protrudes slightly from the needle carrier 400. The rear surface of the shoulder 435 faces away from the sharpened tip of the needle tip 420. The needle tip 420 and the needle holder 415 are engaged such that the needle tip body 440 is held in place by frictional forces when the needle carrier 400 is extended forward. The needle tip body 440 is released from the needle holder 415 when the needle carrier 400 is retracted from a catch. This is facilitated by dimensioning the shoulder 435 so as to be retained by the catch 260 when the needle carrier 400 exits the catch 260. The interaction of the needle carrier 400 and various catches is described in greater detail with respect to FIGS. 5A and 5B.

Figure 5A:
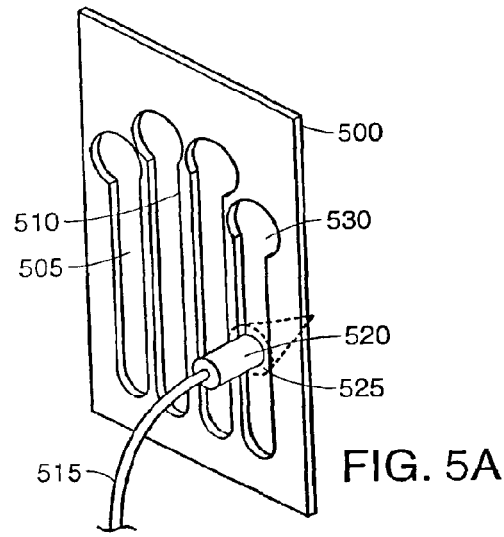
FIGS. 5A and 5B are perspective views of an alternate catch mechanism with a suture carrier.
Figure 5B:
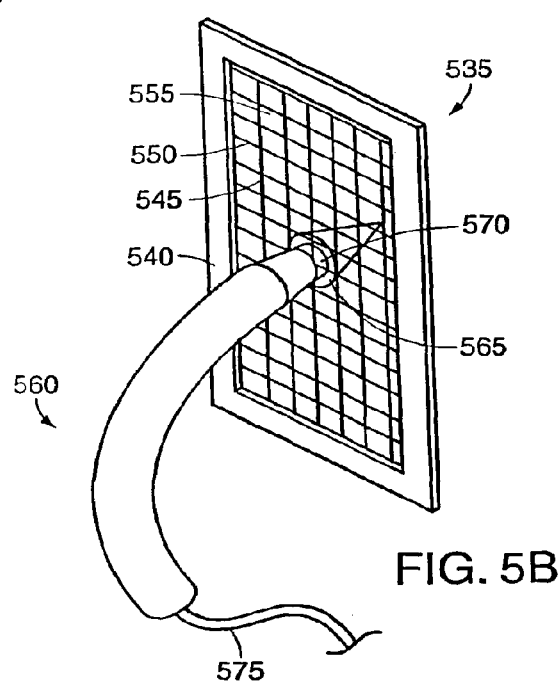

FIGS. 5A and 5B depict alternate catches and illustrate their operation. Referring to FIG. 5A, the catch 500 includes a series of openings 505 defined by successive ribs 510. The catch 500 receives a needle carrier (not shown) and a suture 515 with a needle tip 520 through opening 505, the ribs 510 deflecting slightly to allow the suture carrier and needle tip 520 to pass through. After the needle tip shoulder 525 has cleared the ribs 510 and the suture carrier has been withdrawn, thereby releasing the needle tip 520, the ribs 510 spring back to their original position defining the openings 505. The openings 505 are chosen to be smaller in dimension than the needle tip shoulder 525. This causes the catch 500 to retain the needle tip 520 because, due to the flat rear surface of the tip shoulder 525, needle tip 520 cannot pass back through an opening 505. When it is necessary to remove the needle tip 520 from the catch 500, it may be moved toward an enlarged portion 530 of opening 505; enlarged portion 530 is sized to allow the needle tip shoulder 525 to pass through without resistance. The catch 500 is preferably constructed of thin stainless steel of high temper, such as ANSI 301 full hard. The catch 500 may be fabricated by means of stamping, laser machining, or chemical etching.

Referring now to FIG. 5B, a catch 535 includes a frame 540 to which is attached a woven mesh 545. Threads 550 creating the woven mesh 545 may be nylon, polyester, or the like woven in a common over/under pattern. The weaving of the threads 550 creates windows 555 in the mesh through which a needle carrier 560 may be passed. The needle carrier 560 is constructed such that the shoulder 565 of the needle tip 570 is larger than the windows 555, or conversely, threads 550 are woven such that the windows 555 are smaller than the needle tip shoulder 565. The needle tip 570 of the needle carrier 560 pushes the threads 550 aside, allowing the needle tip shoulder 565 to pass through the holes 555. Upon withdrawal of the needle carrier 560, the threads 550 return to their original positions and the catch 535 retains the needle tip 570 and attached suture 575 (once again due to the flat rear surface of tip shoulder 565, which is larger in size than the windows 555).

Figure 6:
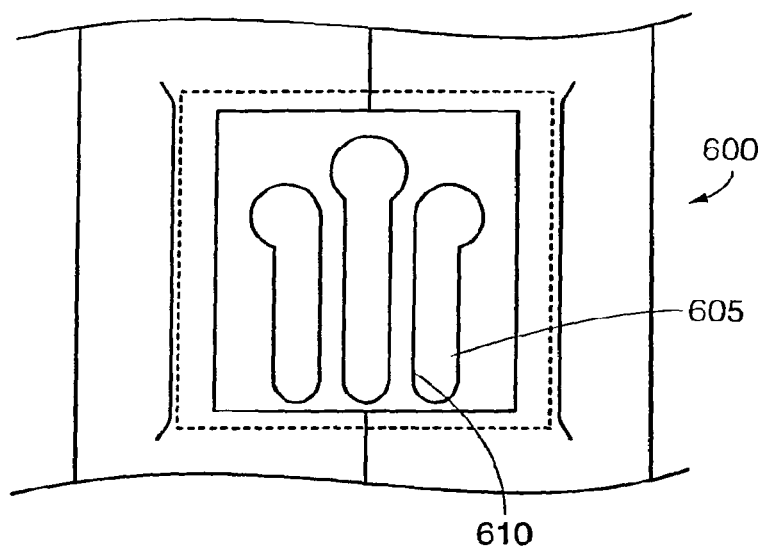
FIG. 6 is an end view illustrating the formed suture tip catch.
Figure 7:
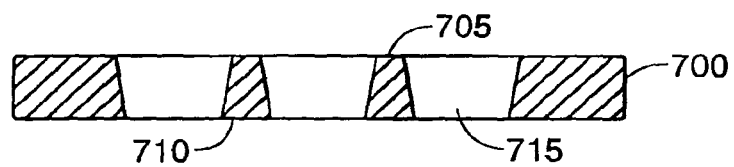
FIG. 7 is a cross-sectional view of the suture tip catch shown in FIG. 6.

Referring to FIG. 6, the catch 600 includes openings 605 defined by ribs 610. The configuration and function of the formed tip catch 600 is similar to that described earlier with respect to FIG. 5A. When the catch 600 is fabricated by means of chemical etching, the preferred method is to etch from a single side, a technique known in the art as single sided etching. When the catch 700 is etched from a single side, the ribs 705 have a tapered cross section 710 as shown in FIG. 7. The tapered cross section 710 helps to guide the needle tip 520 of the needle carrier into the catch openings 715, thereby minimizing the chance of the sharpened end of the needle tip 520 hitting the top of the ribs 705.

Figure 8A:
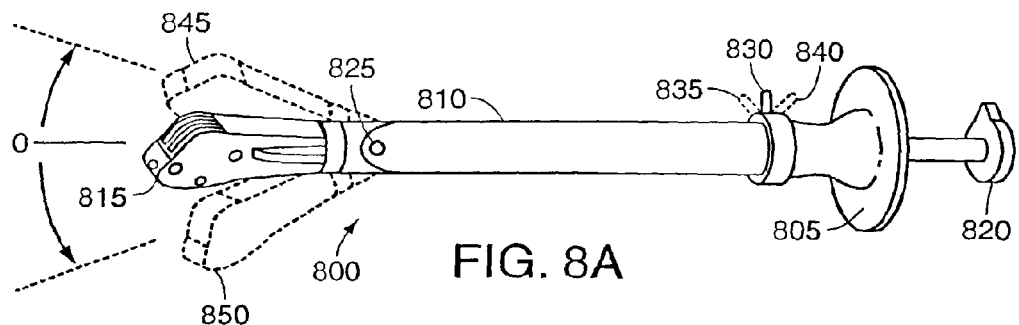
FIGS. 8A-D are perspective views of the general structure of an embodiment of the present invention.

FIGS. 8A-D depict an alternative embodiment of a suturing device 800, which includes a handle 805, an elongate body housing 810, a distal tip 815, an actuator button 820, a pivot joint 825, and a distal tip deflection control lever 830. In FIG. 8A, the control lever 830 is mechanically linked to the distal tip 815 by a cranking assembly that allows the movement of the control lever 830 from a forward position 835 to a back position 840 to cause the deflection of the distal tip 815 about a pivot joint 825 from a tip up position 845 to a tip down position 850.

Figure 8B:
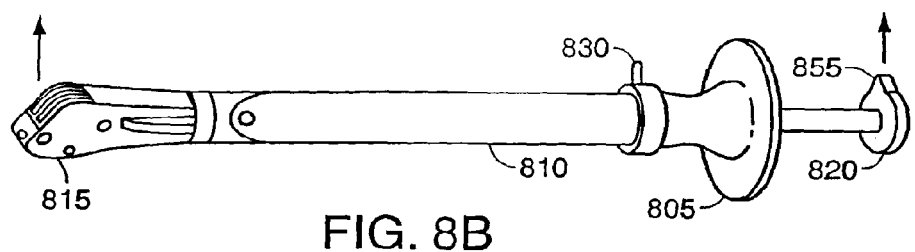
Figure 8C:
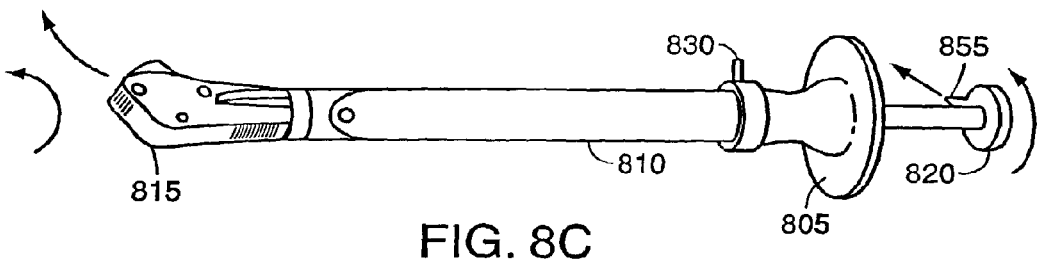
Figure 8D:
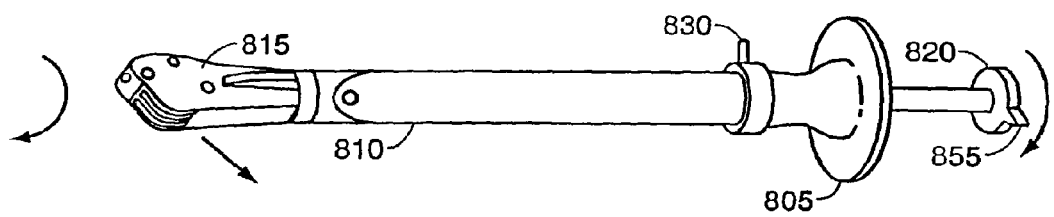

Moreover, distal tip 815 may be rotatable about the axis of the elongate body housing 810 as shown in FIGS. 8B-8D. For example, an actuator button 820 may be secured to the distal tip 815 through housing 815. Rotation of the actuator button 820 causes a corresponding rotation of the distal tip 815. The actuator button 820 may include a directional indicator 855 such as a pointed shape on the actuator button 820 that is aligned with the plane in which the needle tip (not shown) travels during deployment of the device 800. FIGS. 8C and D depict the rotation of the distal tip 815 by 90 degrees in alternative directions from the starting position depicted in FIG. 8B. Additionally, the range of rotation of the distal tip 815 may include a complete 360 degrees about the axis of the elongate body housing 810.

Current surgical methods of treating hypermobility in women include bone anchoring or suture placements by invasive techniques. Hypermobility in women can be relieved by a minimally invasive surgical method that involves passing a suture into the pelvic floor and tightening the suture in order that the pelvic floor buckles or otherwise shortens in length. A suturing device as described above may be used to access the pelvic floor through a small anterior vaginal incision. The end of the distal tip of a suturing device can be pressed against the pelvic floor and a suture can be thrown. The suture can be tightened manually or by a surgical device know in the art. Although this description relates to a specific application, i.e., shortening the pelvic floor via a transvaginal approach, it is to be understood that the principles and construction herein described may be applied to other areas of the human body, and for other procedures requiring suturing body structures.

Figure 9A:
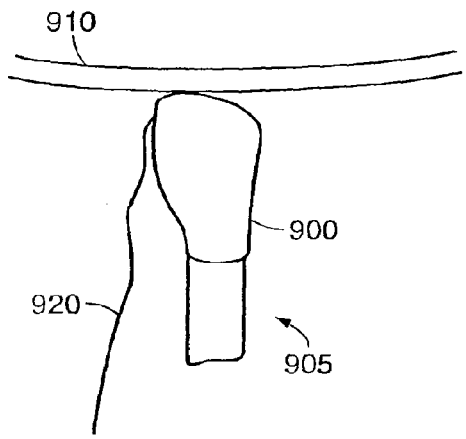
FIGS. 9A-D illustrate a single suture-pass surgical method.
Figure 9B:
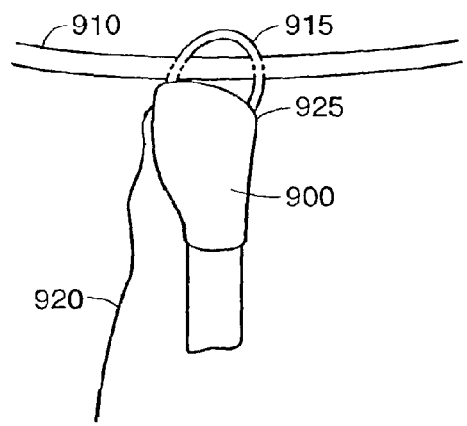
Figure 9C:
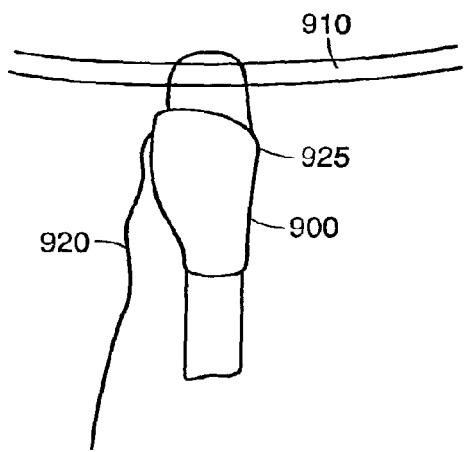
Figure 9D:
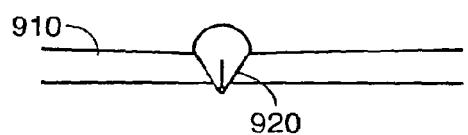

FIGS. 9A-D depict a surgical method for treating hypermobility in women. The surgical method includes positioning the distal tip 900 of a surgical device 905 (partially shown) against the surface of the pelvic floor 910 (FIG. 9A) and deploying the device so that the needle carrier 915, which is carrying a needle tip (not shown) with an attached suture 920, moves in the direction of the arrow and pierces the pelvic floor 910 (FIG. 9B). The path of motion of the needle carrier makes two passages of the tissue of the pelvic floor 910. The needle carrier 915 carries a needle tip into the needle catch 925 in the distal tip 900. In FIG. 9C the needle carrier 915 is retracted into the distal tip 900, the needle tip is retained in the needle catch 925 and the distal tip 900 is retracted from the surface of the pelvic floor 910. The suture 920 remaining in the pelvic floor 910 (FIG. 9C) is tightened and tied thus causing the buckling an effective shortening of the pelvic floor 910 (FIG. 9D).

FIGS. 10A-F depict a surgical method for treating hypermobility in women involving the passing of two sutures into the pelvic floor. The surgical method includes placing the distal tip 1000 of a surgical device 1005 (partially shown) against the surface of the pelvic floor 1010 and deploying the device so that the needle carrier 1015, which is carrying a needle tip 1020 with an attached suture 1025, moves in the direction of the arrow and pierces the pelvic floor 1010 (FIG. 10A). The needle carrier 1015 carries a needle tip 1025 into the needle catch 1030 in the distal tip 1000. In FIG. 10B the needle carrier 1015 is retracted into the distal tip 1000, and while the needle tip is retained in the needle catch 1030 the distal tip 1000 is retracted from the surface of the pelvic floor 1010. The needle tip 1020 is extracted from the needle catch 1030 (FIG. 10B) and reloaded into the needle carrier 1015 (FIG. 10C). In FIG. 10D the suture 1025 is placed in the pelvic floor 1010 in a second location a certain distance from the first suture placement. In FIG. 10E the needle carrier 1015 is retracted into the distal tip 1000, and the needle tip is retained in the needle catch 1030. The retention of the needle tip 1020 in the needle catch 1030 allows for the retention and control of the leading end of the suture 1025 while the distal tip 1000 is refracted from the surface of the pelvic floor 1010 (FIG. 10E). In FIG. 10F the suture 1025 remaining in the pelvic floor 1010 is tightened and tied thus causing the buckling and effective shortening of the pelvic floor 1010. The distance between the two suture placements is directly proportional to the degree to which the pelvic floor 1010 can be shortened. The degree to which the pelvic floor 1010 is shortened can also be controlled by how tightly the suture 1025 is drawn in and tied.

Having described certain embodiments of the invention, it will be apparent to those of ordinary skill in the art that other embodiments incorporating the concepts disclosed herein can be used without departing from the spirit and the scope of the invention. Accordingly, the described embodiments are to be considered in all respects only as illustrative and not restrictive.

What is claimed is:

1. A suturing instrument comprising:
   an elongate body member defining a longitudinal axis having a proximal end portion and a distal end portion, the distal end portion defining a needle catch and a needle exit port, the needle exit port being open in a distal direction; and
   a needle deployment system at least partially disposed within the elongate body member and configured for distally deploying a needle out of the needle exit port, the needle deployment system comprising a linear drive rod and a needle carrier coupled to the linear drive rod via a linking member:
   the needle carrier configured to hold the needle which has a tissue penetrating tip;
   the linking member comprising a rotational element coupled to a second member;
   the rotational element mechanically coupled to the drive rod such that movement of the drive rod causes rotation of the rotational element; and
   the rotation of the rotational element translates into movement of the second member to distally deploy the needle carrier out of the needle exit port to deliver the needle into the needle catch.

2. The suturing instrument of claim 1, wherein the needle deployment mechanism further comprises an actuator for axially moving the linear drive rod within the elongate body member.

3. The suturing instrument of claim 1, wherein the elongate body member further includes a handle disposed opposite the distal portion, the handle at least partially housing the actuator.

4. The suturing instrument of claim 1, wherein at least a portion of the elongate body member is configured to bend in one or more directions relative to the longitudinal axis.

5. The suturing instrument of claim 1, wherein the needle catch defines at least one opening configured to receive a shoulder of the tissue penetrating tip of the needle.

6. The suturing instrument of claim 1, wherein the distal end portion is configured for positioning of target tissue between the needle exit port and the needle catch.

* * * * *